US009494777B2

United States Patent
Rumyantsev et al.

(10) Patent No.: US 9,494,777 B2
(45) Date of Patent: Nov. 15, 2016

(54) MULTI-FOCI LASER SCANNING MICROSCOPE AND USE OF SAME FOR ANALYZING SAMPLES

(71) Applicant: The Board of Trustees of the Leland Stanford Junior University, Palo Alto, CA (US)

(72) Inventors: Oleg Rumyantsev, Stanford, CA (US); Mark Schnitzer, Palo Alto, CA (US); Jerome Anthony-Jean Lecoq, Menlo, CA (US); Tong Zhang, Palo Alto, CA (US); Hyun Kim, Menlo Park, CA (US); Joan Savall, Palo Alto, CA (US)

(73) Assignee: The Board of Trustees of the Leland Stanford Junio, Palo Alto, CA (US)

( * ) Notice: Subject to any disclaimer, the term of this patent is extended or adjusted under 35 U.S.C. 154(b) by 147 days.

(21) Appl. No.: 14/466,262

(22) Filed: Aug. 22, 2014

(65) Prior Publication Data

US 2015/0053870 A1    Feb. 26, 2015

Related U.S. Application Data

(60) Provisional application No. 61/868,631, filed on Aug. 22, 2013.

(51) Int. Cl.
*G02B 21/06* (2006.01)
*G02B 21/00* (2006.01)
*G02B 21/16* (2006.01)
*G01N 21/64* (2006.01)

(52) U.S. Cl.
CPC ......... *G02B 21/002* (2013.01); *G01N 21/6458* (2013.01); *G02B 21/16* (2013.01)

(58) Field of Classification Search
CPC .................................................. G02B 21/002
See application file for complete search history.

(56) References Cited

U.S. PATENT DOCUMENTS

| 7,170,598 | B2 | 1/2007 | Walla et al. | |
|---|---|---|---|---|
| 2006/0012872 | A1* | 1/2006 | Hayashi | G01N 21/21 359/386 |
| 2010/0171866 | A1* | 7/2010 | Brady | G02B 3/0056 348/340 |

* cited by examiner

*Primary Examiner* — David Porta
*Assistant Examiner* — Edwin Gunberg
(74) *Attorney, Agent, or Firm* — Kaplan Breyer Schwarz & Ottesen, LLP

(57) ABSTRACT

A multi-foci laser scanning microscope generates a set of time-multiplexed beams that are simultaneously scanned over multiple scan areas of the sample to be observed. A photodetector array associated with the beams detect fluorescence signals from the sample. A processor processes output signals from the photodetector array based on the time-multiplexing of the beams to provide a much wider field of view and reduced crosstalk between neighboring scan areas for more accurate imaging.

28 Claims, 7 Drawing Sheets

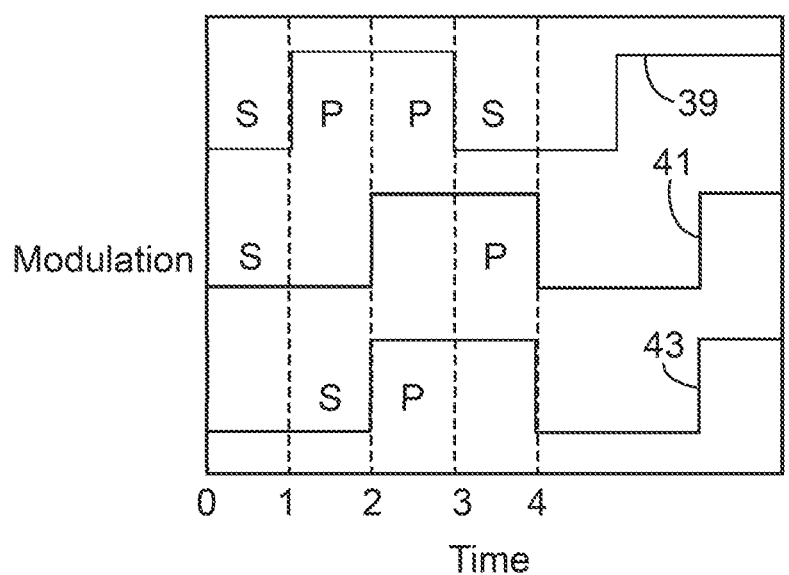

Fig. 4A
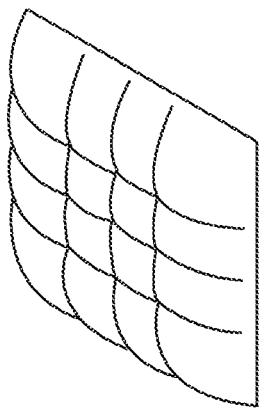
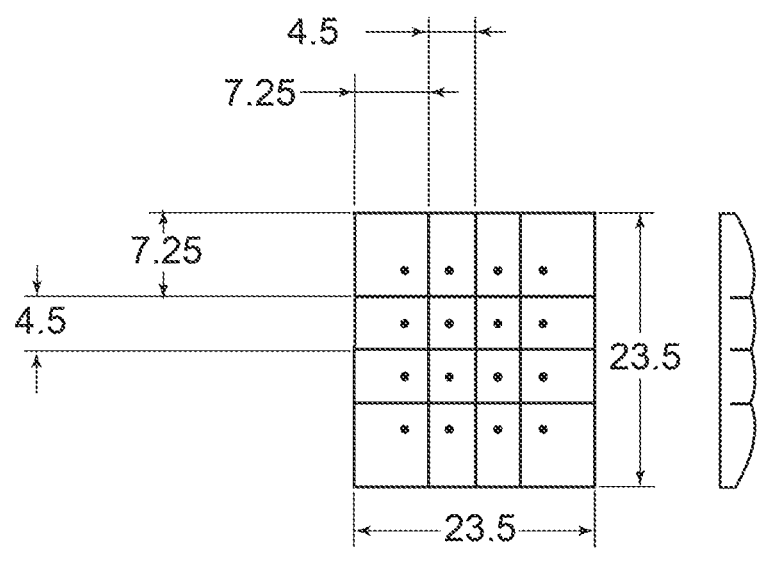
Fig. 4B

MULTI-FOCI LASER SCANNING MICROSCOPE AND USE OF SAME FOR ANALYZING SAMPLES

CROSS-REFERENCE TO RELATED APPLICATION

This application claims priority under 35 U.S.C. 119(e) to U.S. Provisional Application No. 61/868,631, filed Aug. 22, 2013, which is incorporated by reference herein.

FIELD OF THE INVENTION

The present invention relates to a laser scanning microscope, and more particularly to a multi-foci laser scanning microscope having time-multiplexed beams.

BACKGROUND OF THE INVENTION

A conventional multi-photon laser scanning microscope has a rather small field of view on the order of 500 micron (0.5 mm) by 500 micron (0.5 mm). The small field of view means the scanning area is also small. To increase the scanning area, a multi-foci microscope that scans multiple locations at the same time for simultaneous detection by multiple photo detectors have been proposed. An example of this type of microscope is disclosed in U.S. Pat. No. 7,170,578, which is incorporated herein by reference.

However, a major limitation with those types of multi-foci microscopes is that as a scan point nears the boundary of the scan area, crosstalk with neighboring scan areas causes inaccuracies in imaging. Therefore, it would be desirable to provide a multi-foci microscope with more accurate imaging.

SUMMARY OF THE DISCLOSURE

A laser scanning microscope according to an aspect of the present invention includes a laser generator, beam scanner, objective lens, photodetector and a processor.

The laser generator generates a plurality of time-multiplexed beams. The beam scanner scans the plurality of beams across a sample to be observed. The objective focuses the plurality of beams from the beam scanner on to the sample and the photodetector detects fluorescence signals from the sample. The processor reads and processes output signals from the photodetector based on the time-multiplexing of the plurality of beams. The multiplexing of beams provides the advantage of a much wider field of view than was previously possible and reduced crosstalk between neighboring scan areas for more accurate imaging.

According to another aspect of the present invention, a method of analyzing a sample by measuring fluorescence signals is provided. A laser generator generates a plurality of time-multiplexed beams which are focused onto and scanned across the sample. In certain embodiments, multiple non-neighboring scan areas are illuminated at the same time during a given phase in an illumination cycle. The fluorescence signals from the sample are detected using a photodetector having a plurality of detector elements. The output signals from the photodetector are processed based on the time-multiplexing of the plurality of beams. Advantageously, the method of analyzing the sample using multiplexed beams allows a much wider field of view than was previously possible and reduced crosstalk between neighboring scan areas for more accurate imaging.

BRIEF DESCRIPTION OF THE DRAWINGS

FIG. 2B is a graph of control signals for controlling electro-optic polarization modulators in the microscope of FIG. 1.

FIG. 4A is a perspective view of a lens array for the microscope of FIG. 1.

FIG. 4B show a plan view and side view of the lens array of FIG. 4A.

DETAILED DESCRIPTION OF INVENTION

Throughout the present teachings, any and all of the one, two, or more features and/or components disclosed or suggested herein, explicitly or implicitly, may be practiced and/or implemented in any combinations of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

The present invention is designed to allow simultaneous collection of fluorescence signals in one very large field of view of 2 mm×2 mm or larger with the capability to adjust imaging depth depending on the position in the field of view to accommodate scanning on a curved surface. For example, the present invention can be used to record simultaneous neural activity in a brain on a curved surface corresponding to the brain curvature with minimal crosstalk with neighboring areas. Recording from about 10000 neurons in cortex of a head-fixed rodent can be achieved with the present invention.

Figure 1:
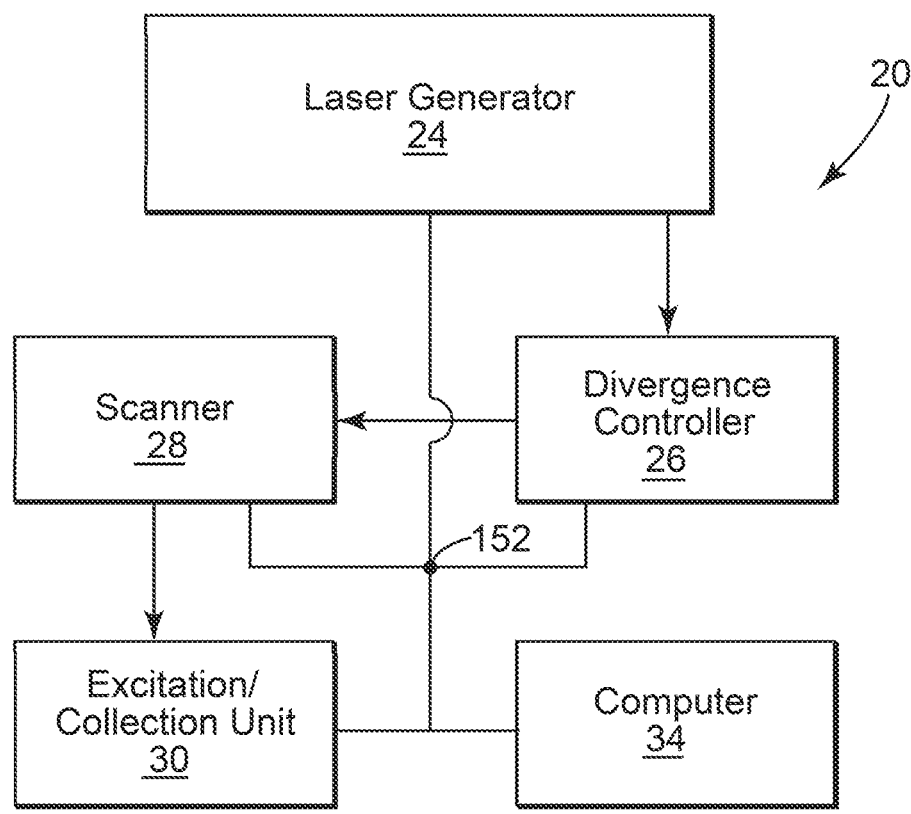
FIG. 1 is a functional diagram of a multi-foci laser scanning microscope according to an aspect of the present invention.

One embodiment of the present invention is illustrated in FIG. 1. A two-photon laser scanning microscope 20 of the present invention includes a laser generator 24 that generates a plurality of beams A-P that are temporally multiplexed into 4 phases, a divergence controller 26 positioned in the optical path of the plurality of beams to adjust the focal depths of the plurality of beams, a beam scanner 28 that scans the plurality of beams A-P across a sample 32 to be observed, and an excitation/collection unit 30 that illuminates the sample and collects fluorescence signals coming from the sample. The above components are connected and controlled by a processor 146 and associated program module 154 in a computer 34 (see FIG. 5) through a common communication link 152. Each component will now be explained in greater detail.

Figure 2A:
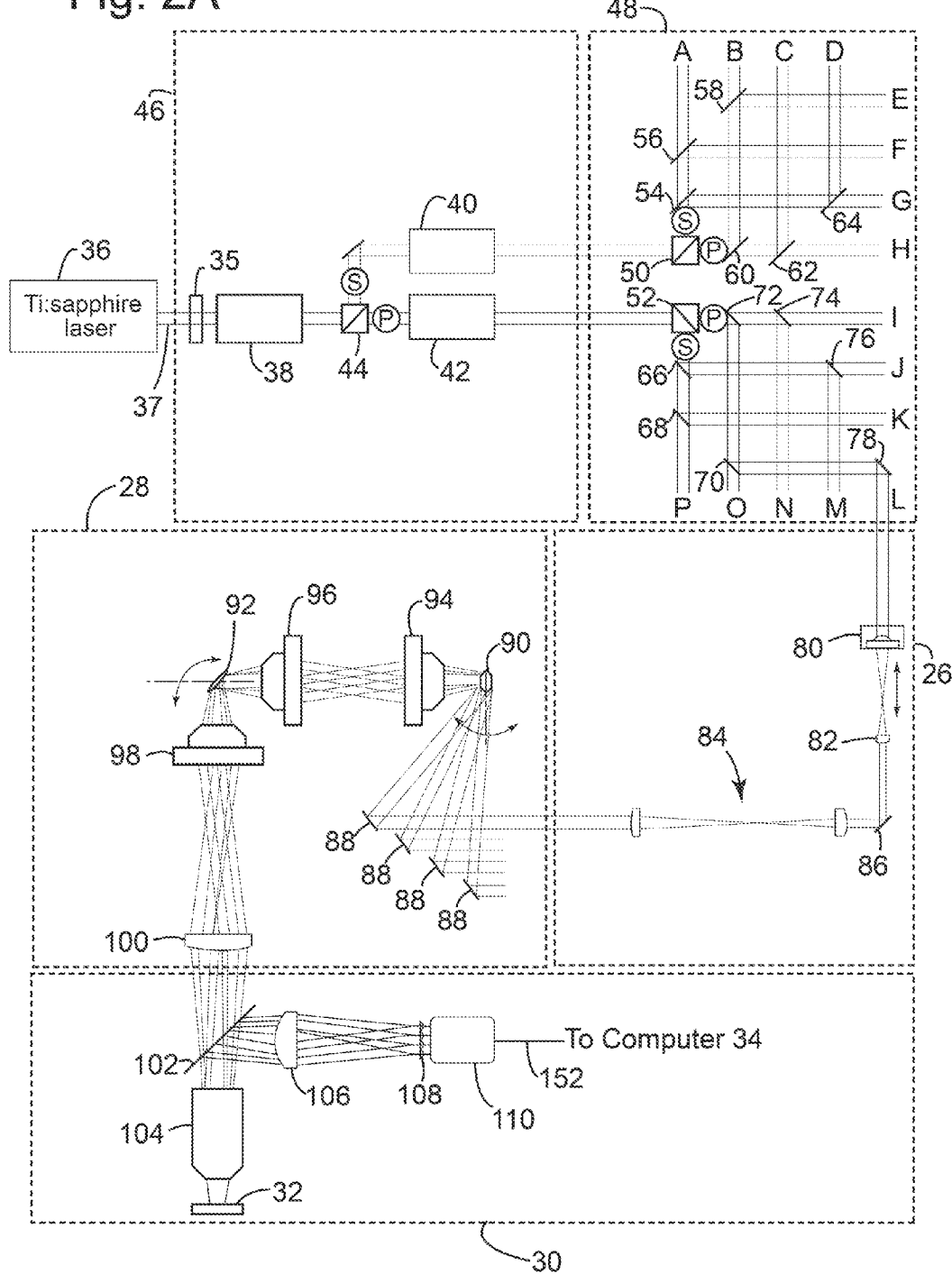
FIG. 2A is a detailed diagram of the laser scanning microscope of FIG. 1.

The laser generator 24 includes a laser source 36 that generates an ultrafast (i.e., pulse duration in the order of a picosecond or less) pulsed laser beam 37. In the embodiment shown, the laser is an 80 MHz Ti:sapphire laser having a 100 femtosecond pulse width. The laser beam 37 is then temporally multiplexed by a temporal multiplexer 46. The multiplexer 46 uses a combination of electro-optic polarization modulators 38,40,42 and a polarizing beamsplitter 44 according to a time multiplexing pattern as shown in FIG. 2B. The polarizing beamsplitter 44 reflects S polarized beam to the modulator 40 and passes P polarized beam to the modulator 42.

When imaging neuronal activity in brains of live animals, it is important to limit the amount of laser power incident on the brain tissue. When performing a raster scan with an array of laser beams due to overshot of beams (due to turn-around time of the galvo scanner), there is extra non-useful laser power incident on the sample at the end of a horizontal scan. It can be harmful to the sample. To address this issue, an optical chopper 35 having a duty cycle of 90% is positioned in the optical path of the main beam 37 to blank the main laser beam. The duty cycle should match the duty cycle of the particular type of galvo scanner being used.

The time multiplexing is done under the control of the computer 34. As shown in FIG. 2B, each cycle of the time-multiplexing pattern has four phases and control signals 39, 41 and 43 from the computer 34 control the electro-optic modulators 38, 40 and 42, respectively. Specifically, during the four phases, the modulator 38 outputs a beam having a polarization of S, P, P and S, respectively while each of the modulators 40 and 42 outputs a beam having a polarization of S, S, P and P, respectively.

However, during the first phase, the modulator 42 provides no beam output since the polarizing beam splitter 44 receives no P polarized beam from the modulator 38. During the second phase, the modulator 40 provides no beam output since the polarizing beam splitter 44 receives no S polarized beam from the modulator 38. During the third phase, the modulator 40 provides no beam output since the polarizing beam splitter 44 receives no S polarized beam from the modulator 38. During the fourth phase, the modulator 42 provides no beam output since the polarizing beam splitter 44 receives no P polarized beam from the modulator 38.

In sum, the output of the modulator 40 during the four cycles is respectively S, X, X, P, where X means no beam output while the output of the modulator 42 is respectively X, S, P, X.

The outputs of the modulators 40 and 42 are fed into a beam divider 48. The beam divider 48 includes a combination of polarizing beamsplitters 50,52 and plate beamsplitters 54-78 that are positioned at selected angles to generate an M by N rectangular array of beamlets (A through P). Each plate beamsplitter splits the beam equally into 50% each. Thus, the laser generator 24 as a whole achieves a spatial and temporal multiplexing of the beams. It is also important to note that since each beamlet is generated through exactly two plate beamsplitters, the intensity of each beamlet is at 25% of the original beam 37, rather than 1/16 of the original beam intensity if it were to be divided into 16 simultaneous beamlets. This type of multiplexing scheme allows efficient use of laser power due to the quadratic dependence of two-photon excitation efficiency on incident power and allows a single laser to be used.

In the embodiment shown, M=4 and N=4. Thus, the beam divider 48 generate a 4 by 4 square array of beamlets. However, M and N can be any number greater than 1 so long as some of the beamlets are time-multiplexed relative to the others.

The beamlets (AP) are then fed into 16 divergence controllers 26, one for each beamlet. However, for clarity, only one divergence controller is shown. The divergence controller 26 includes a set of electrically tunable lens 80 and an offset lens 82, which is reflected into a 1:2 telescope 84 by a reflector 86.

Each divergence controller 26 controls the focal depth of the associated beamlet and is individually controllable by the computer 34. The controllers 26 allow the microscope 20 to adjust the focal depth of individual beamlets to account for the different topography/contour of the sample, and also scan the sample at different depths to create an image stack for 3-D imaging by the computer 34.

To eliminate vignetting, the plane of constant beam size is imaged onto the mirrors/reflectors 88 by the 1:2 telescope 84 which uses a long focal length and low magnification. Thus, the size of the beams on scanning mirrors 90,92 does not change while their divergence can be individually controlled. Group delay dispersion compensation scheme is used to account for propagation of beams through significantly thick optical elements.

The divergence adjusted beamlets enter the scanner 8 and are reflected by reflectors 88 into a vertical scanner 90. Although there are a total of 16 reflectors 88, only 4 reflectors are shown for clarity.

The beamlets are then reflected by the vertical scanning mirror 90 onto a pair of telecentric F-Theta lenses 94,96 and then to a horizontal scanning mirror 92. The horizontal and vertical scanners 90,92 are single axis scanning mirrors positioned in conjugate optical planes by the 1:1 telescope formed by the lenses 94,96. The lenses 94,96 have longer focal length and larger apertures to accommodate a wider field of view. Another F-Theta lens 98 and tube lens 100 maps the horizontal scanning mirror on the back aperture of a high numerical aperture objective lens 104.

Figure 3:
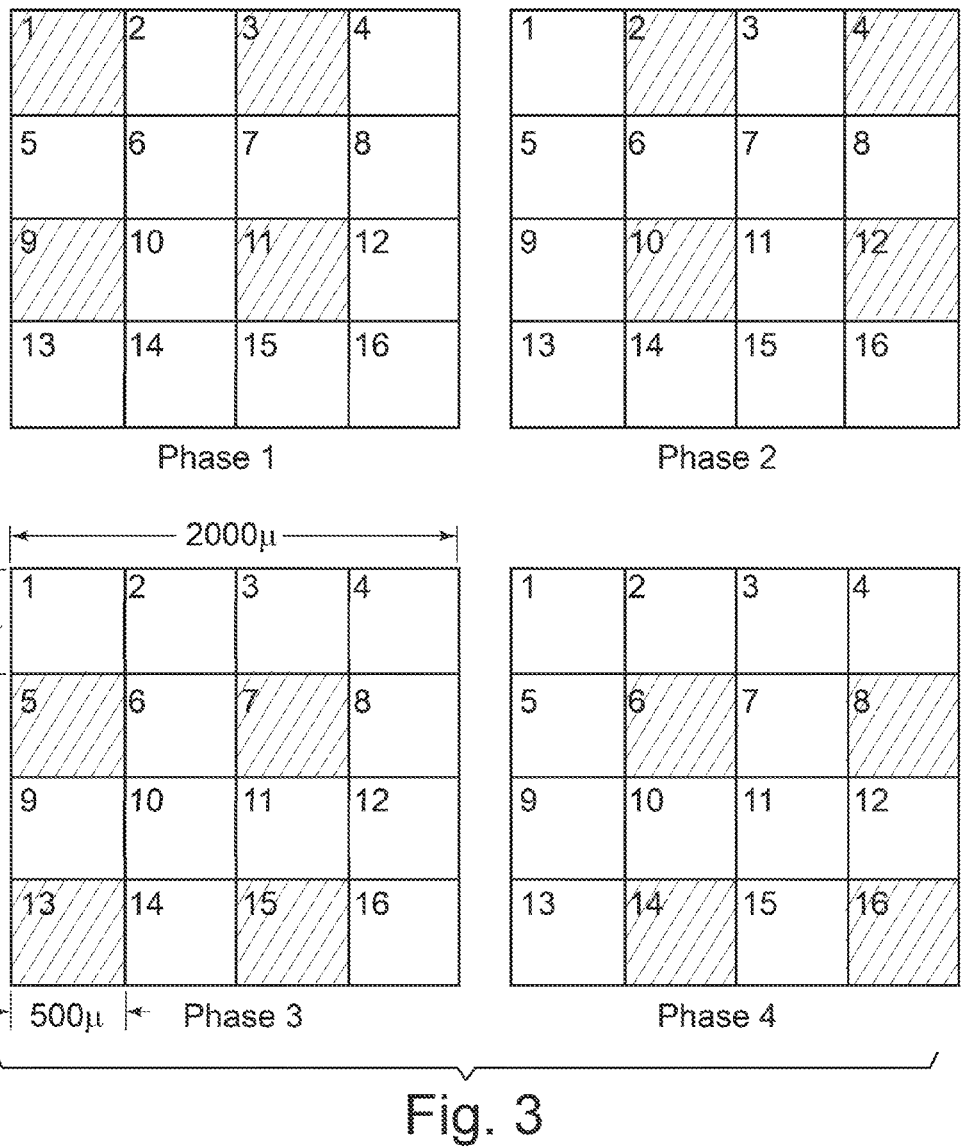
FIG. 3 illustrates detection of multiple scan areas with time-multiplexed beams.

As can be seen in FIG. 3, the 16 beamlets A-P are focused into a square pattern in the sample by the objective 104 while only 4 beamlets reach the sample in 4 non-neighboring sub-field of view (scan areas) at any given phase and excite fluorescence simultaneously at the focal point. For each scan point (pixel), beamlets from all four phases are illuminated on the sample in an interleaved manner before the scanner 28 moves on to the next scan point. Thus, during each cycle, all 16 sub-field of views (16 scan areas) are illuminated at the corresponding scan point.

The dichroic splitter/filter 102 reflects the fluorescence signals (e.g., 520-540 nm signals which are shorter than the excitation wavelengths) from the sample towards a collection lens (achromatic doublet) 106 which focuses the fluorescence signals onto the back focal plane of a lens array 108 of M by N lenses. In the embodiment shown, the lens array 108 is a 4 by 4 array. The lens array 108 then focuses the fluorescence signals towards the center of each detector element (1-16) of a photodetector array 110, where the detector elements are the most sensitive. The photodetector array is, for example, Hamamatsu PMT H8711-300 extended green photocathode. Accordingly, an optical axis of each lens in the array is aligned with the center of the associated detector element. In the embodiment shown, the photodetector array 110 is an array of 4 by 4 detector elements. The output of the photodetector is then read in accordance with the multiplexed beamlets as shown in FIG. 3 and the following table.

TABLE 1

| Phase | beamlet-detector | beamlet-detector | beamlet-detector | beamlet-detector |
|---|---|---|---|---|
| 1 | A-1 | D-3 | F-9 | G-11 |
| 2 | J-2 | K-4 | M-10 | P-12 |
| 3 | I-5 | L-7 | N-13 | O-15 |
| 4 | B-6 | C-8 | E-14 | H-16 |

Each box represents a sub-field of view (one of 16 scan areas) covered by an associated beamlet as well as a detector element associated with that beamlet. For example, the top left box (box 1) represents a 500 micron by 500 micron sub-field of view (scan area) associated with detector element 1 and beamlet A.

If each scan point is an area on the order of 1 micron by 1 micron, the vertical and horizontal scanners 90,92 would scan 500 points per line for 500 lines for a total scan points of 250,000 in each sub-field of view.

As persons of ordinary skill in the art would appreciate, if all 16 scan areas are illuminated and detected at the same time, the detector elements 1-16 would have difficulty distinguishing whether the fluorescence signal originated from the respective scan area especially as the scan point approaches the boundary locations between two scan areas. Often, due to scattering of fluorescence in the sample and crosstalk, the signal may have come from a neighboring scan area.

According to the principle of the present invention, this problem is solved by multiplexing the beamlets into 4 different phases by space and time. This way, in each phase, no neighboring scan area (thus no neighboring detector element) is simultaneously detected.

FIG. 3 illustrates this concept. All under the control of the computer 34, in phase 1, only detector elements 1, 3, 9 and 11 are detected; in phase 2, only detector elements 2, 4, 10 and 12 are detected; in phase 3, only detector elements 5, 7, 13 and 15 are detected; and in phase 4, only detector elements 6, 8, 14 and 16 are detected. As can be seen, in any phase, for each detector element being detected, output from any neighboring detector elements are not read and can be ignored by the computer 34.

Alternatively and more preferably, however, output from neighboring detector elements can be detected and such output can be attributed to a different scan area by the computer 34 depending on what part of the scan area is being scanned/excited at the time and its proximity to the center of the neighboring detector elements, and what phase the beams are in.

For example, assume that the scan point being excited in the sample is in the lower right corner of the sub-field of view (scan area) in phase 1. In that case, detector elements 1,3,9,11 would be active as shown in FIG. 3. According to the invention, rather than ignoring outputs from detector elements 2,5,6, they can be read by the computer 34. The issue then become to what scan area those signals should be attributed. Since the distance from the center of detector elements 2,5,6 are closest to the scan point (lower right corner) of scan area 1, those signals from detector elements 2,5,6 can be attributed to scan area 1. For the same reasons, outputs from detector elements 4,7,8 can be attributed to scan area 3 (detector element 3) while outputs from detector elements 10,13,14 can be attributed to scan area 9 (detector element 9) and outputs from detector elements 12,15,16 can be attributed to scan area 11 (detector element 11).

As another example, assume that the scan point being excited in the sample is in the upper left corner of the sub-field of view (scan area) in phase 1. Output from detector element 2 would be attributed to scan area 3, output from detector element 6 would be attributed to detector element 11 while output from detector element 5 would be attributed to detector element 9 based on the distance from the scan point to the center of each detector element.

FIGS. 4A and 4B illustrate a novel lens array according to an aspect of the present invention. When the scanners 90,92 are scanning a boundary location in the field of view, much of the fluorescence signals hitting the outer lenses (corresponding to detector elements 1-5, 8-9 and 12-16) can be lost. To capture additional signals, the outer lenses are made larger than the inner lenses (corresponding to detector elements 6,7,10,11) as shown in FIG. 4A. Even though the outer lenses are larger than the inner lenses, the optical axis would still be aligned with the center of the associated detector elements in the detector array 110.

The inner lenses have a square dimension of 4.5 mm by 4.5 mm while the outer lenses (corner lenses) have a dimension of 7.25 mm by 7.25 mm and outer lenses (corresponding to detector elements 2,3,8,12,14 and 15) disposed between the corner lenses have a dimension of 7.25 mm by 4.5 mm. Corners of the corner lenses can be rounded (such as R=0.3 mm).

Figure 5:
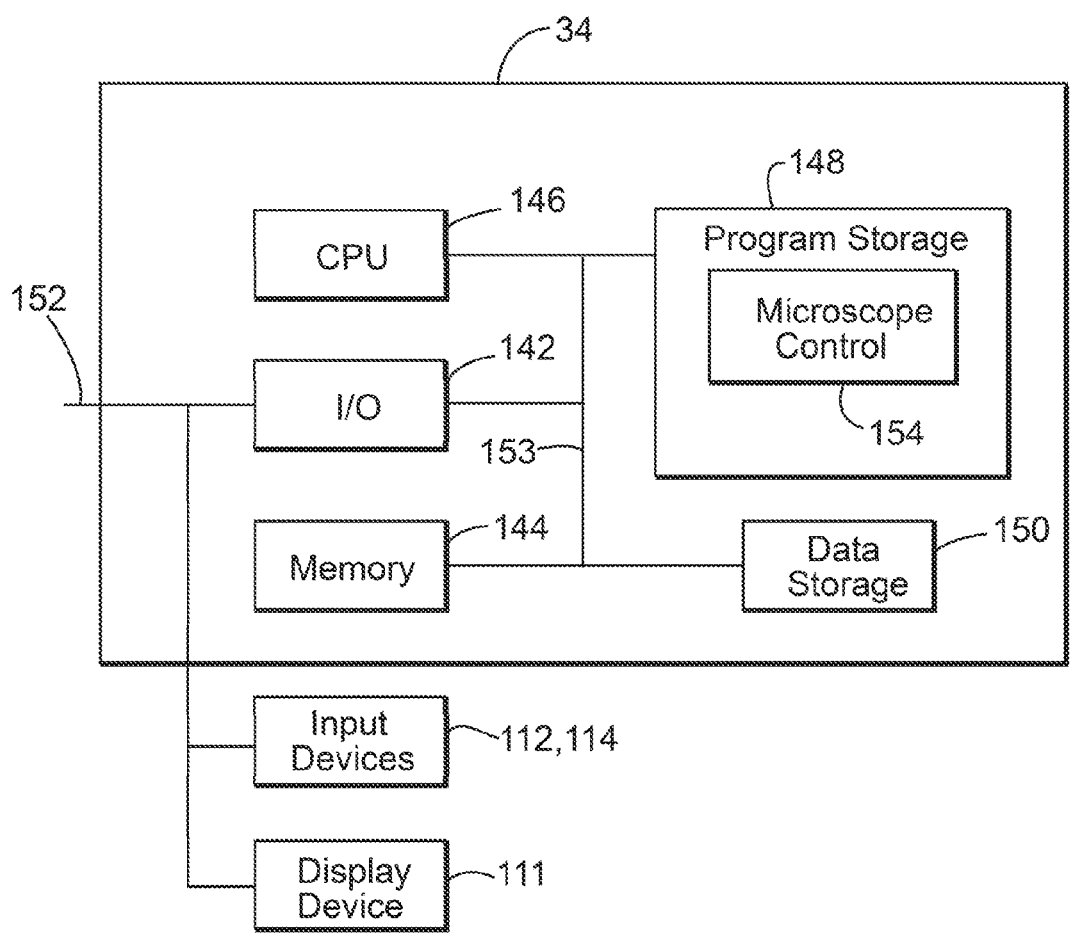
FIG. 5 is a schematic diagram of a computer that controls various components of the microscope of FIG. 1 and performs signal processing of outputs from the detector array of the microscope of FIG. 1.
Figure 6:
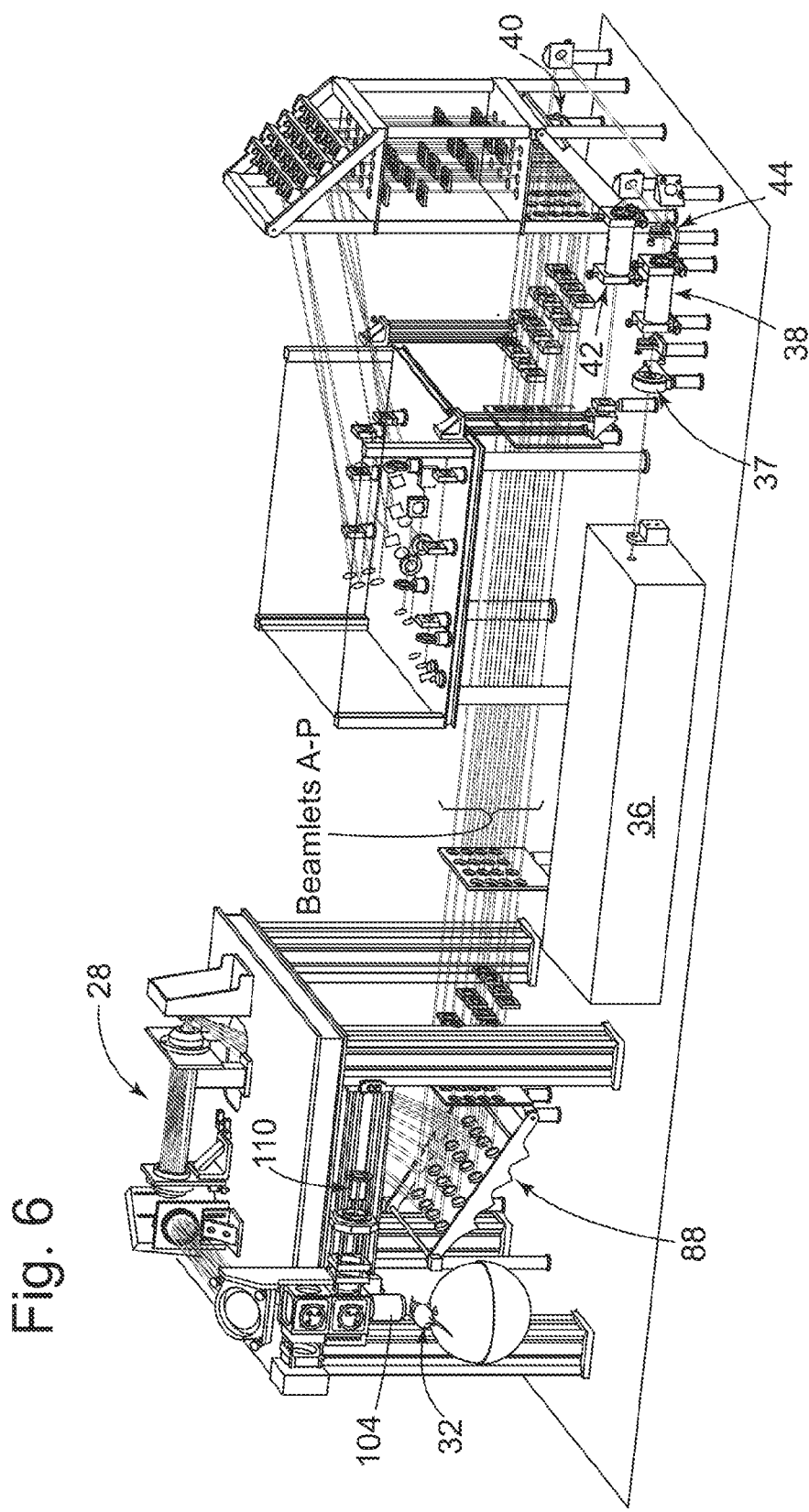
FIG. 6 is a diagram of a working microscope according to an aspect of the present invention.

Referring now to FIG. 5, the computer 34 of the present invention can be used to control operation of the microscope 20 including controlling all electrically controllable components to excite and collect signals, and also to perform signal processing of signals from the photodetector 110. Preferably, one computer is used to control the microscope operation and another computer is used to perform the signal processing. Alternatively, one computer can be used for both functions.

The computer 34 is connected to the communication link 152 through an I/O interface 142 such as a USB (universal serial bus) interface, which receives information from and sends information over the communication link 152. The computer 34 includes memory storage 144 such as RAM, processor (CPU) 146, program storage 148 such as ROM or EEPROM, and data storage 150 such as a hard disk, all commonly connected to each other through a bus 153. The program storage 148 stores, among others, a microscope control module 154 which includes a user interface module that interacts with the user in planning for and scanning the sample 32 and collecting the results through the photodetector array 110. Any of the software program modules in the program storage 148 and data from the data storage 150 can be transferred to the memory 144 as needed and is executed by the CPU 146.

As stated above, typically, another more powerful computer with similar components as the computer 34 would be used to process signals coming from the photodetector 110. In that case, a signal processing module 154 would be stored in the program storage 148 and the CPU 146 would likely include a general purpose processor as well as a digital signal processor for processing the received fluorescence signals into images in conjunction with the signal processing module 154.

Applications of the present invention include in-vivo neural activity imaging, generic fluorescence imaging, optical stimulation, cardio-vascular imaging and muscle imaging, among others. Advantageously, the microscope 20 according to the present invention, allows simultaneous imaging in 16-fold larger area than what is possible under the conventional technology while maintaining a relatively high 10 Hz image update frequency. Implementation of individual control of imaging depth in each sub-field of view allow imaging on a curved surface in the specimen. Spatiotemporal multiplexing allows a significant reduction of crosstalk between neighboring scan areas of the total field of view in multi-foci multi-photon microscopy. Objective lens is custom coated for maximum transmission at both excitation and fluorescence wavelengths to ensure maximum performance.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed is:

1. A laser scanning microscope comprising:
    a laser generator that generates a plurality of time-multiplexed N by M beams in an illumination cycle having a plurality of phases, wherein N and M are each at least 2;
    a beam scanner that scans the plurality of beams across a sample to be observed;
    an objective that focuses the plurality of beams from the beam scanner on to the sample;
    a photodetector including an array of N by M detector elements respectively associated with the time multiplexed N by M beams, the photodetector detecting fluorescence signals from the sample; and
    a processor coupled to the photodetector and operable to process output signals from the photodetector according to the illumination cycle such that in any phase, only output signals from non-neighboring detector elements are read.

2. The laser scanning microscope of claim 1, wherein the laser generator includes:
    a laser source that generates a primary laser beam;
    a beam divider that divides the primary laser beam into a plurality of beamlets.

3. The laser scanning microscope of claim 2, wherein the laser generator includes at least one electro-optic modulator that selectively modulates the polarity of the primary laser beam within each illumination cycle.

4. The laser scanning microscope of claim 3, wherein the laser generator includes:
    a first electro-optic modulator that selectively modulates the polarity of the primary laser beam within the illumination cycle;
    a polarizing beam splitter that splits the output of the first electro-optic modulator into first and second outputs respectively having S and P polarizations;
    second and third electro-optic modulators respectively connected to the first and second outputs of the polarizing beam splitter and operable to selectively modulate the polarity of the split light beams from the first second outputs of the polarizing beam splitter.

5. The laser scanning microscope of claim 1, wherein the laser generator includes:
    a laser source that generates a primary laser beam;
    a beam divider having at least one polarizing beam splitter and a plurality of plate beam splitters positioned at an angle to incident beams, the beam divider dividing the primary laser beam into a plurality of beamlets with each beamlet having the same power as the other beamlets.

6. The laser scanning microscope of claim 1, wherein the processor detects fluorescence signals from the detector elements based on the phase of the illumination cycle and location of the scan point being illuminated.

7. The laser scanning microscope of claim 1, wherein the processor detects fluorescence signals from:
    the detector elements associated with the phase of the illumination cycle; and
    neighboring detector elements based on the proximity of the scan point being illuminated to the neighboring detector elements.

8. The laser scanning microscope of claim 1, further comprising a divergence controller positioned in the optical path of the plurality of beams to adjust the focal depths of the plurality of beams.

9. The laser scanning microscope of claim 1, wherein the number of the plurality of beams equals K and the divergence controller includes K electrically tunable lenses that are individually controllable.

10. The laser scanning microscope of claim 1, wherein the photodetector includes an M by N array of detector elements, further comprising an M by N lens array that focuses the fluorescence signals on the respective detector elements, wherein outer lenses are larger in size than inner lenses in the lens array.

11. The laser scanning microscope of claim 1, wherein the photodetector includes an M by N array of detector elements, further comprising an M by N lens array that focuses the fluorescence signals on the respective detector elements, wherein outer lenses are larger in size than inner lenses in the lens array and an optical axis of each of the outer lenses is aligned with the center of the associated detector element.

12. A multi-photon, multi-foci laser scanning microscope comprising:
    a laser generator that generates a plurality of M by N time-multiplexed beams in an illumination cycle having a plurality of phases, wherein M>2 and N>2;
    a beam scanner that scans the plurality of beams across a plurality of scan areas of the sample to be observed, wherein at least two scan areas are simultaneously illuminated, but are non-neighboring scan areas;
    an objective that focuses the plurality of beams from the beam scanner on to the sample;
    a photodetector array having an M by N detector elements respectively associated with the M by N beams, the detector elements detecting fluorescence signals from the sample; and
    a processor coupled to the photodetector array and operable to process output signals from the detector elements according to the illumination cycle such that in any phase, only output signals from non-neighboring detector elements are read.

13. The laser scanning microscope of claim 12, further comprising a divergence controller positioned in the optical path of the plurality of beams to adjust the focal depths of the plurality of beams.

14. The laser scanning microscope of claim 12, wherein during each illumination cycle, the processor detects fluorescence signals from the detector elements based on the phase of the illumination cycle.

15. The laser scanning microscope of claim 12, wherein the processor detects fluorescence signals from:
    the detector elements associated with the phase of the illumination cycle; and
    neighboring detector elements based on the proximity of the scan point being illuminated to the neighboring detector elements.

16. The laser scanning microscope of claim 12, further comprising an M by N lens array that focuses the fluorescence signals on the respective detector elements, wherein outer lenses are larger in size than inner lenses in the lens array and an optical axis of each of the outer lenses is aligned with the center of the associated detector element.

17. A method of analyzing a sample by measuring fluorescence signals comprising:
generating a plurality of time-multiplexed N by M beams in an illumination cycle having a plurality of phases, wherein N and M are each at least 2;
focusing the plurality of beams on to the sample;
scanning the focused plurality of beams across the sample;
detecting, using a photodetector having an array of N by M detector elements respectively associated with the time multiplexed N by M beams, fluorescence signals from the sample; and
processing output signals from the photodetector according to the illumination cycle such that in any phase, only output signals from non-neighboring detector elements are read.

18. The method of claim 17, wherein the step of generating includes:
generating a primary laser beam;
dividing the primary laser beam into the plurality of time-multiplexed beamlets.

19. The method of claim 18, wherein the step of generating a plurality of beamlets includes selectively modulating the polarity of the primary laser beam within each illumination cycle with an electro-optic modulator.

20. The method of claim 19, wherein the step of generating a plurality of beamlets includes:
selectively modulating the polarity of the primary laser beam within each illumination cycle;
splitting the selectively modulated primary laser beam into an S polarized beam and P polarized beam;
selectively modulating the polarization of the S polarized beam and P polarized beam.

21. The method of claim 17, wherein the step of generating a plurality of beamlets includes:
generating a primary laser beam;
dividing the primary laser beam into a plurality of beamlets with each beamlet having the same power as the other beamlets.

22. The method of claim 17, wherein the step of detecting includes detecting fluorescence signals from the detector elements based on the phase of the illumination cycle and location of the scan point being illuminated.

23. The method of claim 17, wherein the step of detecting fluorescence signals from:
the detector elements associated with the phase of the illumination cycle; and
neighboring detector elements based on the proximity of the scan point being illuminated to the neighboring detector elements.

24. The method of claim 17, further comprising adjusting the focal depths of the plurality of beams to account for the contour of the sample being examined.

25. The method of claim 17, further comprising focusing the plurality of beams onto the detector elements through a lens array, wherein the outer lenses are larger in size than inner lenses in the lens array.

26. A laser scanning microscope comprising:
a laser generator that generates a plurality of time-multiplexed beams;
a beam scanner that scans the plurality of beams across a sample to be observed;
an objective that focuses the plurality of beams from the beam scanner on to the sample;
a photodetector including first and second detector elements respectively associated with first and second beams of the plurality of beams, the photodetector detecting fluorescence signals from the sample;
a processor coupled to the photodetector and operable to process output signals from the photodetector based on the time-multiplexing of the plurality of beams; and
a divergence controller positioned in the optical path of the plurality of beams to adjust the focal depths of the plurality of beams.

27. The laser scanning microscope of claim 26, wherein:
the laser source generates N by M beams as the plurality of beams, wherein N>1 and M>1; and
the photodetector array includes an N by M detector elements, wherein during each illumination cycle, the processor detects fluorescence signals from detector elements based on the phase of the illumination cycle.

28. The laser scanning microscope of claim 26, wherein the photodetector includes an M by N array of detector elements, further comprising an M by N lens array that focuses the fluorescence signals on the respective detector elements, wherein outer lenses are larger in size than inner lenses in the lens array and an optical axis of each of the outer lenses is aligned with the center of the associated detector element.

* * * * *